US00PP28577P2

(12) United States Plant Patent
Nishita et al.

(10) Patent No.: US PP28,577 P2
(45) Date of Patent: Oct. 24, 2017

(54) ***PORTULACA* PLANT NAMED 'SAKPOR010'**

(50) Latin Name: *Portulaca oleracea*
Varietal Denomination: SAKPOR010

(71) Applicant: Sakata Seed Corporation, Yokohama (JP)

(72) Inventors: Koichi Nishita, Kakegawa (JP); Michiyoshi Fuyama, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 14/999,127

(22) Filed: Mar. 31, 2016

(51) Int. Cl.
*A01H 5/02* (2006.01)

(52) U.S. Cl.
USPC ..... Plt./471

(58) Field of Classification Search
USPC ..... Plt./471
See application file for complete search history.

*Primary Examiner* — Annette Para
(74) *Attorney, Agent, or Firm* — Bethany R. Roahrig; Barbara Campbell; Cochran Freund & Young, LLC

(57) ABSTRACT

A *portulaca* plant particularly distinguished by having rose flowers with yellow eyes, long flower blooming period and a dense and mounding plant growth habit, is disclosed.

2 Drawing Sheets

Genus and species: *Portulaca oleracea.*
Variety denomination: 'SAKPOR010'.

BACKGROUND OF THE NEW PLANT

The present invention comprises a new and distinct variety of *portulaca* plant, botanically known as *Portulaca oleracea*, and referred to by the variety name 'SAKPOR010'.

'SAKPOR010' originated from a hybridization made in October 2009 in Kakegawa, Japan. The female parent was an unpatented proprietary *Portulaca* breeding line named '7B1-8A-V1' which had a red flower color and a semi-upright plant growth habit. The male parent was an unpatented proprietary *Portulaca* breeding line named '7B1-4A-V1', characterized by its pink flower color and domed plant growth habit.

In October 2009, '7B1-8A-V1' and '7B1-4A-V1' were crossed and some $F_1$ seeds were obtained. In May 2010, the $F_1$ seed was sown in the greenhouse, cultivated, and plant lines were produced. In August 2010, three plants were selected from the $F_1$ group. In October 2010, $F_2$ seeds were collected after crossing within the three plants. In August 2011 plant line 'K2012-133' was selected for its rose flower color, long flower blooming period and domed plant growth habit.

In March 2012, line 'K2012-133' was vegetatively propagated, cultivated, and evaluated. In August 2012 the breeder confirmed that line 'K2012-133' was fixed and stable. The line 'K2012-133' was propagated and cultivated again in 2013 and 2014 to reconfirm the lines' stability. The line was subsequently named 'SAKPOR010' and its unique characteristics were found to reproduce true to type in successive generations of asexual propagation.

SUMMARY

The following are the most outstanding and distinguishing characteristics of this new variety when grown under normal horticultural practices in Salinas, Calif.

1. Rose flower color with yellow eye;
2. Long flower blooming period; and
3. A dense and mounding plant growth habit.

CROSS REFERENCE TO RELATED APPLICATIONS

Plant Breeder's Rights for 'SAKPOR010' were applied for in Japan on Sep. 9, 2014 (Application number 29523). 'SAKPOR010' has not been made publicly available or sold more than one year prior to the filing date of this application.

DESCRIPTION OF THE PHOTOGRAPHS

This *portulaca* plant is illustrated by the accompanying photographs which show the plant's overall plant habit including form, foliage, and flowers. The photographs are of a plant three months old grown in Salinas, Calif. under greenhouse conditions. The colors shown are as true as can be reasonably obtained by conventional photographic procedures.

DESCRIPTION OF THE NEW VARIETY

Figure 1:
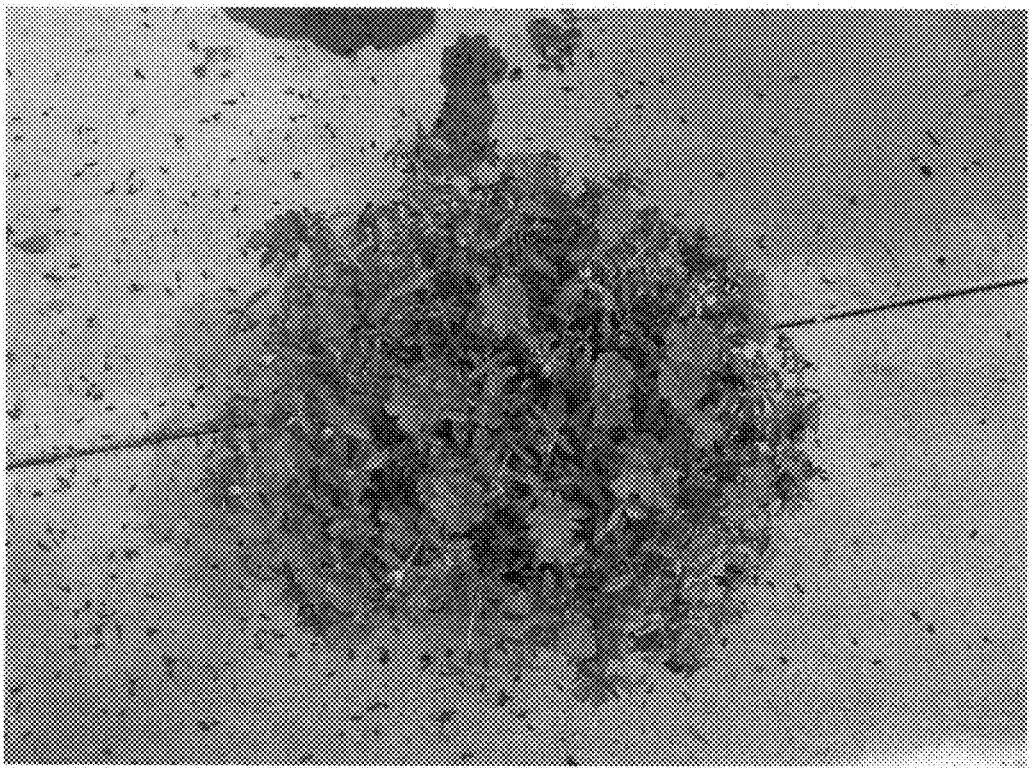
FIG. 1 shows the overall plant habit of the plant grown in a pot.
Figure 2:
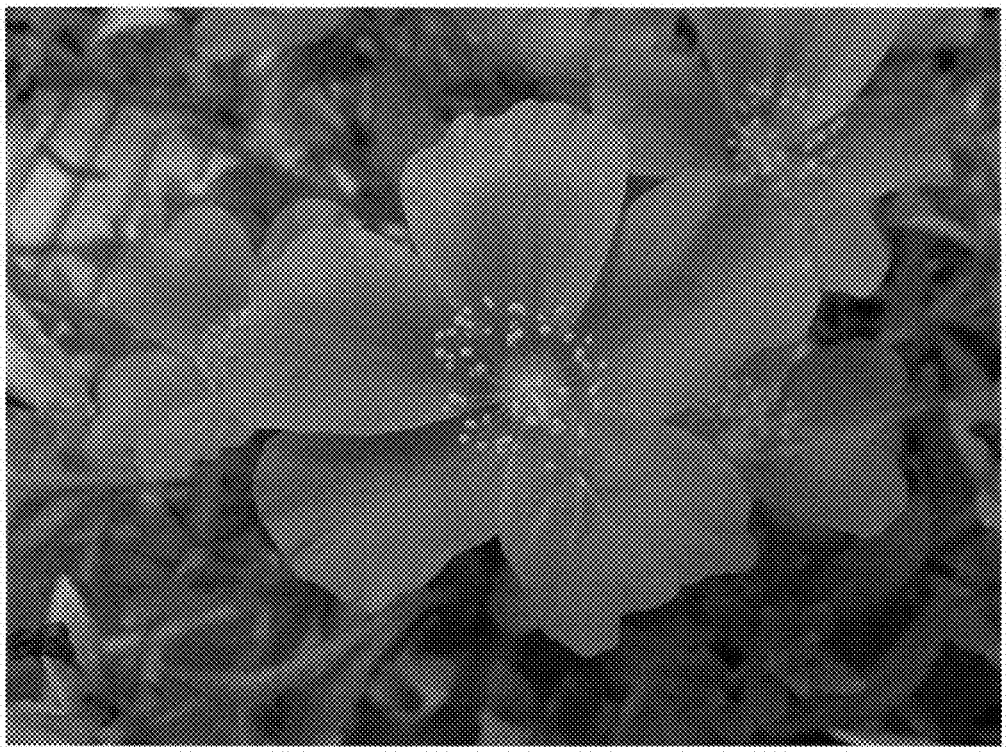
FIG. 2 shows a close-up of the mature inflorescence of the plant.

The following detailed descriptions set forth the distinctive characteristics of 'SAKPOR010'. The data which define these characteristics were collected three month old plants grown in Salinas, Calif. Color references are to The R.H.S. Colour Chart of The Royal Horticultural Society of London (R.H.S.), $4^{th}$ edition (2001).

Classification:

*Family.*—Portulacaceae.
*Botanical.*—*Portulaca oleracea.*
*Common.*—Purslane.
*Designation.*—'SAKPOR010'.

Parentage:
*Female parent.*—'7B1-8A-V1' (unpatented).
*Male parent.*—'7B1-4A-V1' (unpatented).

Growth:
*Time to produce a rooted cutting.*—About 2 weeks.
*Environmental conditions for plant growth.*—The terminal 1.0 to 1.5 inches of an actively growing stem was excised. The vegetative cuttings were propagated in five to six weeks. The base of the cuttings were dipped for 1 to 2 seconds in a 1:9 solution of Dip 'N Grow (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Plant description:
*Habit and form.*—Dense and mounding.
*Height.*—12.0 cm from soil line to top of foliage.
*Spread.*—33.0 cm.
*Time and conditions to produce a rooted cutting.*—2 weeks.
*Life cycle.*—Annual.
*Flowering requirements.*—Blooms repeatedly from spring to fall.

Stems:
*General description.*—Round, slightly rough with lateral ridges.
*Stem color.*—RHS 59B (Red-Purple) with closest to RHS 145C (Yellow-Green).
*Anthocyanin color.*—RHS 59B (Red-Purple).
*Pubescence.*—Absent.
*Stem diameter.*—2.0 mm to 3.0 mm.
*Stem length.*—9.0 cm to 15.0 cm.
*Internode length.*—1.3 cm to 2.0 cm.
*Branching.*—Abundant.

Leaves:
*Arrangement.*—Alternate.
*Shape.*—Oblanceolate.
*Apex.*—Acute.
*Base.*—Rounded.
*Margin.*—Entire.
*Leaf attachment.*—Petiolate.
*Surface appearance (both surfaces).*—Dull, slightly waxy.
*Leaf length.*—2.1 cm.
*Leaf width.*—8.0 mm.
*Leaf thickness.*—Less than 1.0 mm.
*Surface texture (both surfaces).*—Dull, slightly waxy.
*Leaf color.*—Upper surface: RHS 146A (Yellow-Green) with RHS 61A (Red-Purple) at edge. Lower surface: Closest to RHS 147B (Yellow-Green) with RHS 61A (Red-Purple) at edge.
*Leaf surface pubescence.*—Absent.
*Venation.*—Only the mid vein is visible.
*Petiole.*—Absent.
*Fragrance.*—Absent.

Inflorescence:
*Inflorescence type.*—Solitary, sessile.
*Flowering habit.*—Determinate.
*Time to bloom from propagation.*—6 to 8 weeks.
*Lastingness of individual blooms on the plant.*—1 day.
*Flower diameter.*—3.2 cm.
*Flower depth.*—5.0 mm to 8.0 mm.
*Fragrance.*—Absent.

Flower bud:
*Surface appearance and texture.*—Shiny, pubescent.
*Shape.*—Lanceolate.
*Bud length.*—1.0 cm.
*Bud diameter.*—3.0 mm.
*Bud color.*—RHS 144B (Yellow-Green) with RHS 61A (Red-Purple).

Corolla:
*Shape.*—Five distinct petals, free, petals are heart-shaped with a square base.
*Petal pubescence.*—Glabrous.
*Petal size.*—Length: 1.6 cm. Width: 1.2 cm.
*Petal apex.*—Retuse.
*Petal margin.*—Double lobed, slightly sinuate.
*Petal color.*—Upper surface: RHS N74A (Red-Purple) with RHS 47A (Red) towards eye zone; eye zone: RHS 7A (Yellow). Lower surface: RHS N74B (Red-Purple) with RHS 29C (Orange) towards eye zone.

Calyx:
*Arrangement.*—Composed of two sepals, free.
*Sepals.*—Shape: Elliptic. Apex: Cuspidate. Margin: Entire, slightly sinuate. Sepal length: 7.0 mm. Sepal diameter: 4.0 mm. Sepal color: Both upper and lower surfaces are closest to RHS 144B (Yellow-Green), and are translucent. Texture (both surfaces): Soft, dull and slightly tacky. Appearance: Double lobed, slightly sinuate.

Reproductive organs: Androecium.
*Stamen number.*—Many.
*Stamen form.*—Free.
*Stamens color.*—Anther: RHS 17A (Yellow-Orange). Filament color: RHS 12A (Yellow).
*Stamen length.*—3.0 mm to 7.0 mm.
*Pollen amount.*—Abundant.
*Pollen color.*—RHS 17A (Yellow-Orange).
*Fragrance.*—Absent.
*Placental arrangement.*—Central.
*Pistil number.*—1 (per inflorescence).
*Pistil length.*—1.2 cm.
*Stigma color.*—Closest to RHS 59B (Red-Purple).
*Stigma length.*—4.0 mm.
*Style length.*—8.0 mm.
*Style color.*—RHS 59B (Red-Purple) with 1B (Green-Yellow) at point of attachment.
*Seed production.*—Absent.

Disease and insect resistance: None observed.

Environmental conditions, disease and insect resistance: None observed.

COMPARISON WITH PARENTAL LINES AND KNOWN VARIETY

'SAKPOR010' is a distinct variety of *Portulaca* owing to its rose flower color and domed plant habit. 'SAKPOR010' is distinguished from its parents as shown below in Table 1.

TABLE 1

| Comparison with Parental Lines | | | |
|---|---|---|---|
| Characteristic | 'SAKPOR010' | Female parent: '7Bl-8A-V1' | Male parent: '7Bl-4A-V1' |
| Flower color | Rose | Red | Pink |
| Plant growth habit | Domed | Semi-mounding upright | Domed |

'SAKPOR010' is most similar to the variety SUN DANCE 'Rose', also known as 'SAKPOR001' (U.S. Plant Pat. No. 24,528) however, there are differences in flower petal color and plant growth habit as described in the table below.

TABLE 2

| Comparison with Similar Variety | | |
|---|---|---|
| Characteristic | 'SAKPOR010' | SUN DANCE 'Rose' |
| Flower petal color, upper surface | Upper: RHS N74A (Red-Purple) with RHS 47A (Red) towards eye zone | RHS 67A (Red-Purple) |
| Plant growth habit | Domed | Semi-mounding, upright |

We claim:

1. A new and distinct variety of *portulaca* plant named 'SAKPOR010' as illustrated and described herein.

* * * * *